(12) United States Patent
Kozloski et al.

(10) Patent No.: US 11,538,576 B2
(45) Date of Patent: Dec. 27, 2022

(54) ILLUSTRATIVE MEDICAL IMAGING FOR FUNCTIONAL PROGNOSIS ESTIMATION

(71) Applicant: International Business Machines Corporation, Armonk, NY (US)

(72) Inventors: James R. Kozloski, New Fairfield, CT (US); Viatcheslav Gurev, Bedford Hills, NY (US); Tuan M. Hoang Trong, Fairfax, VA (US); Adamo Ponzi, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 458 days.

(21) Appl. No.: 16/653,438

(22) Filed: Oct. 15, 2019

(65) Prior Publication Data
US 2021/0110914 A1  Apr. 15, 2021

(51) Int. Cl.
*G16H 30/40* (2018.01)
*G06N 3/08* (2006.01)
(Continued)

(52) U.S. Cl.
CPC .............. *G16H 30/40* (2018.01); *G06N 3/08* (2013.01); *G16H 50/20* (2018.01); *G16H 50/50* (2018.01)

(58) Field of Classification Search
CPC ........ G16H 50/50; G16H 50/20; G16H 30/40; G06N 3/08
See application file for complete search history.

(56) References Cited

U.S. PATENT DOCUMENTS 9,589,374 B1 * 3/2017 Gao ...................... G06T 11/008
2012/0316862 A1  12/2012 Sultan et al.
(Continued)

FOREIGN PATENT DOCUMENTS

KR  101539923 B1  7/2015
KR  101898575 B1  9/2018

OTHER PUBLICATIONS

Stetka, B. Think of Multiple Sclerosis as a Leaking Swimming Pool. Scientific American. Jun. 18, 2015; pp. 1-8; https://www.scientificamerican.com/article/think-of-multiple-sclerosis-as-a-leaking-swimming-pool-video/ (Year: 2015).*
(Continued)

*Primary Examiner* — Evangeline Barr
*Assistant Examiner* — Jordan L Jackson
(74) *Attorney, Agent, or Firm* — Stephen J. Walder, Jr.; Kristopher L. Haggerty

(57) ABSTRACT

A mechanism is provided in a data processing system comprising at least one processor and at least one memory, the at least one memory comprising instructions that are executed by the at least one processor and configure the at least one processor to implement a medical record to illustrative medical image translation engine. The medical record to illustrative medical image translation engine receives a medical record batch from storage for a patient and generates one or more predicted prognosis records based on the medical record batch using a neural network. The medical record to illustrative medical image translation engine converts the one or more predicted prognosis records to illustrative medical images using a first agent. The medical record to illustrative medical image translation engine generates a presentation of disease progression using the illustrative medical images and outputs the presentation to a user.

20 Claims, 8 Drawing Sheets

(51) Int. Cl.
*G16H 50/50* (2018.01)
*G16H 50/20* (2018.01)

(56) References Cited

U.S. PATENT DOCUMENTS

| | | | | |
|---|---|---|---|---|
| 2015/0023574 | A1* | 1/2015 | Sohn | G06K 9/4604 |
| | | | | 382/131 |
| 2016/0171682 | A1* | 6/2016 | Abedini | G06T 7/0012 |
| | | | | 382/132 |
| 2016/0210749 | A1 | 7/2016 | Nguyen et al. | |
| 2016/0253469 | A1* | 9/2016 | Donovan | G16H 50/20 |
| | | | | 705/2 |
| 2018/0225823 | A1 | 8/2018 | Zhou et al. | |
| 2019/0139270 | A1* | 5/2019 | De Fauw | G06T 11/003 |
| 2019/0197358 | A1* | 6/2019 | Madani | G06T 7/0012 |
| 2020/0160980 | A1* | 5/2020 | Lyman | G06Q 10/06315 |

OTHER PUBLICATIONS

Jung, KH, et al. Review: Deep Learning for Medical Image Analysis: Applications to Computed Tomography and Magnetic Resonance Imaging. Hanyang Med Rev. 2017, vol. 37, pp. 61-70; https://doi.org/10.7599/hmr.2017.37.2.61; pISSN 1738-429X; eISSN 2234-4446. (Year: 2017).*

Guibas, John T. et al., "Synthetic Medical Images from Dual Generative Adversarial Networks", https://arxiv.org/abs/1709.01872, Jan. 8, 2018, 9 pages.

High, Rob, "The Era of Cognitive Systems: An Inside Look at IBM Watson and How it Works", IBM Corporation, Redbooks, Dec. 12, 2012, 16 pages.

Lao, Qicheng, "Leveraging Disease Progression Learning for Medical Image Recognition", https://arxiv.org/abs/1806.10128, Sep. 1, 2018, 6 pages.

Shin, Hoo-Chang et al., "Medical Image Synthesis for Data Augmentation and Anonymization using Generative Adversarial Networks", https://arxiv.org/abs/1807.10225, Sep. 13, 2018, 11 pages.

Stetka, Bret, "Think of Multiple Sclerosis as a Leaking Swimming Pool", https://www.scientificamerican.com/article/think-of-multiple-sclerosis-as-a-leaking-swimming-pool-video/, Jun. 18, 2015, 8 pages.

Tilling, Kate et al., "Modelling disease progression in relapsing-remitting onset multiple sclerosis using multilevel models applied to longitudinal data from two natural history cohorts and one treated cohort", Published in Health Technology Assessment Oct. 2016; vol. 20: No. 81 DOI: 10.3310/hta20810, 8 pages.

Xia, Yingce et al., "Dual Inference for Machine Learning", Proceedings of the Twenty-Sixth International Joint Conference on Artificial Intelligence (IJCAI-17), Aug. 2017, 7 pages.

Xia, Yingce et al., "Dual Learning for Machine Translation", https://arxiv.org/abs/1611.00179, Nov. 1, 2016, 9 pages.

Yi, Xin et al., "Generative Adversarial Network in Medical Imaging: A Review", https://arxiv.org/abs/1809.07294, Sep. 19, 2018, 20 pages.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, 14 pages.

* cited by examiner

//ILLUSTRATIVE MEDICAL IMAGING FOR FUNCTIONAL PROGNOSIS ESTIMATION

BACKGROUND

The present application relates generally to an improved data processing apparatus and method and more specifically to mechanisms for generating illustrative medical images for functional prognosis estimation.

An electronic health record (EHR) or electronic medical record (EMR) is the systematized collection of patient and population electronically-stored health information in a digital format. These records can be shared across different health care settings. Records are shared through network-connected, enterprise-wide information systems or other information networks and exchanges. EMRs may include a range of data, including demographics, medical history, medication and allergies, immunization status, laboratory test results, radiology images, vital signs, personal statistics like age and weight, and billing information.

EMR systems are designed to store data accurately and to capture the state of a patient across time. It eliminates the need to track down a patient's previous paper medical records and assists in ensuring data is accurate and legible. Due to the digital information being searchable and in a single file, EMRs re more effective when extracting medical data for the examination of possible trends and long-term changes in a patient. Population-based studies of medical records may also be facilitated by the widespread adoption of EMRs.

Like any number of industries, healthcare is being transformed by the explosion of low-cost data. In healthcare, the transformation is driven in large part by EMR adoption and digitization. There have been many benefits. End users can take advantage of quantities of newly available information to solve problems in population health, clinical decision support, and patient engagement, among other applications.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, method is provided in a data processing system comprising at least one processor and at least one memory, the at least one memory comprising instructions that are executed by the at least one processor and configure the at least one processor to implement a medical record to illustrative medical image translation engine. The method comprises receiving, by the medical record to illustrative medical image translation engine, a medical record batch from storage for a patient. The method further comprises generating, by the medical record to illustrative medical image translation engine, one or more predicted prognosis records based on the medical record batch using a neural network. The method further comprises converting, by the medical record to illustrative medical image translation engine, the one or more predicted prognosis records to illustrative medical images using a first agent. The method further comprises generating, by the medical record to illustrative medical image translation engine, a presentation of disease progression using the illustrative medical images, and outputting, by the medical record to illustrative medical image translation engine, the presentation to a user.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
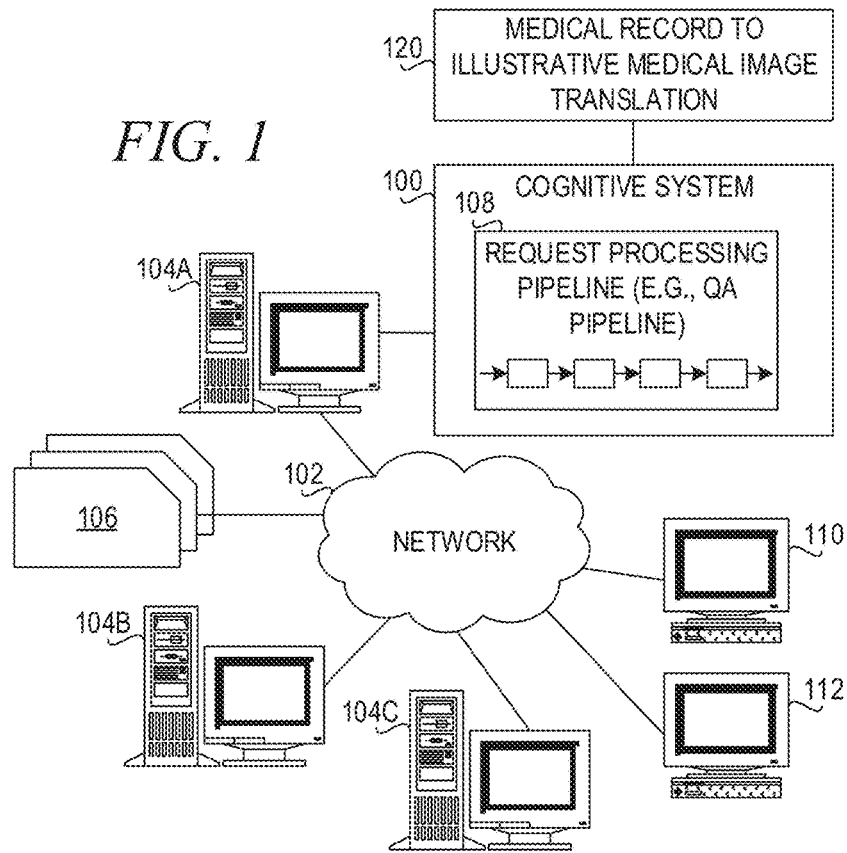
FIG. 1 depicts a schematic diagram of one illustrative embodiment of a cognitive healthcare system in a computer network.

Hidden nervous system states are difficult to predict diagnose, and explain to patients. In particular, multiple sclerosis (MS) states responsible for flare-ups among patients suffering from the relapsing-remitting form of this disease (rr-MS) are not detectable using standard medical imaging. Therefore, models have been proposed to illustrate how these hidden states evolve, becoming manifest on brain images, and lead to debilitating patient MS symptoms. One such model is the leaking swimming pool model in which hidden states are illustrated as mounds that grow and shrink at different points in a swimming pool at various pool depths. Because the level of water in the pool is also changing, the model does a good job of explaining how multiple factors contribute to manifestation of symptoms in relapsing-remitting MS.

Illustrating underlying pathophysiological causes and dynamics has been attempted in rr-MS using the leaking swimming pool model, but not with a formal translational aspect from medical records to simulated medical images. Instead, doctors have used adhoc illustrations, such as the leaking swimming pool model to simply adjust parameters until the model is suggestive of patient state and imaging results.

The illustrative embodiments propose the use of a dual neural machine translation (d-NMT) system to parameterize this model of relapsing-remitting MS based on patient medical records, thereby allowing a better illustration for patients of the dynamics of their condition, as well as a model of patient-specific pathophysiology that can be augmented as additional data on mechanisms become available.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular features or elements present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention me described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carryout combinations of special purpose hardware and computer instructions.

Figure 2:
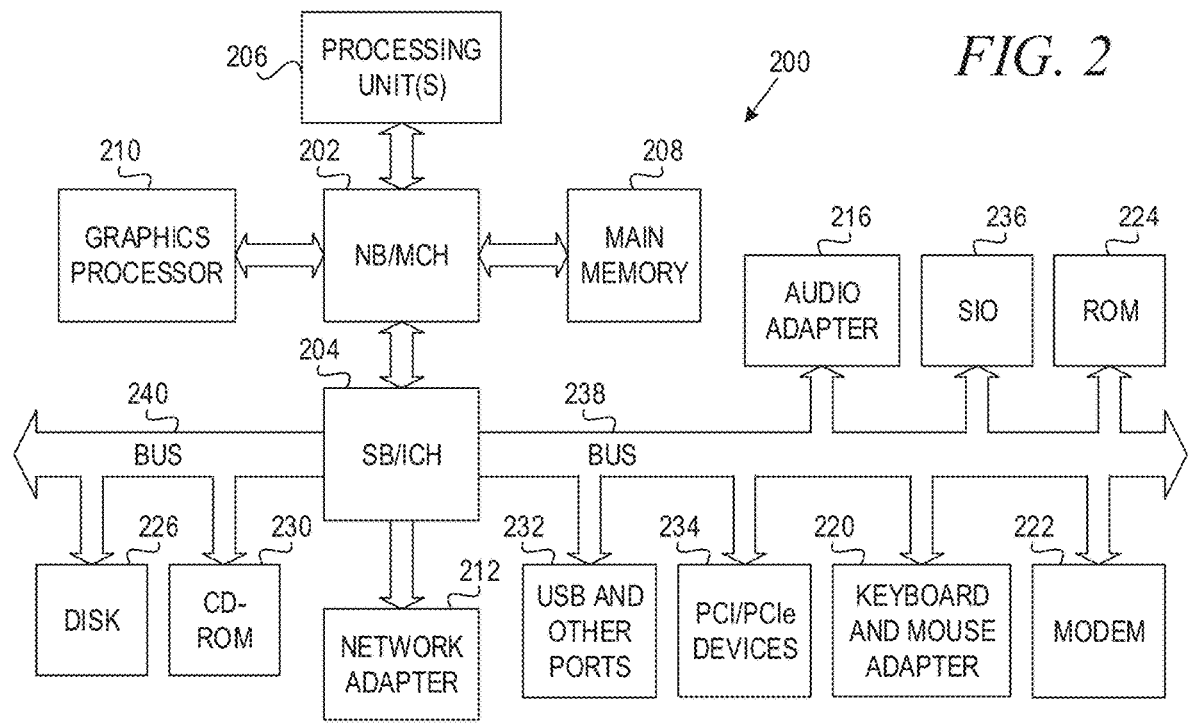
FIG. 2 is a block diagram of an example data processing system in which aspects of the illustrative embodiments are implemented.
Figure 3:
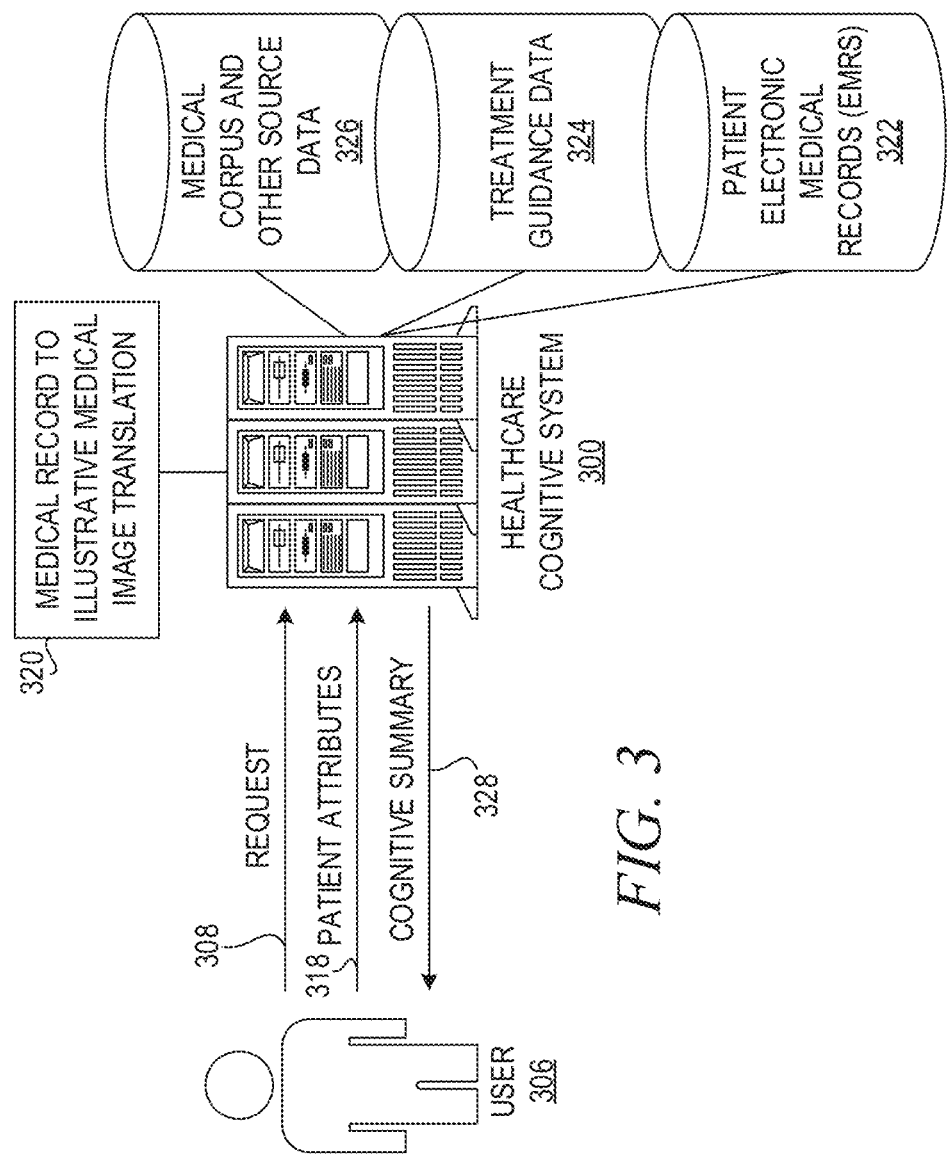
FIG. 3 is an example diagram illustrating an interaction of elements of a healthcare cognitive system in accordance with one illustrative embodiment.

As noted above, the present invention provides mechanisms for generating health care clinical data-controlled datasets. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have its own associated corpus or corpora that it ingests and operates on, e.g., one corpus for blood disease domain documents and another corpus for cancer diagnostics domain related documents in the above examples. These corpora may include, but are not limited to, EMR data and other historical patient data.

As will be discussed in greater detail hereafter, the illustrative embodiments may be integrated in, augment, and extend the functionality of these QA pipeline, or request processing pipeline, mechanisms of a healthcare cognitive system with regard to illustrative artificial intelligence for functional prognosis estimation. Thus, it is important to rust have an understanding of how cognitive systems are implemented before describing how the mechanisms of the illustrative embodiments are integrated in and augment such cognitive systems and request processing pipeline mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108, which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process may be repeated for each of the candidate responses to generate a ranked listing of candidate responses, which may then be presented to the user that submitted the input request, e.g., a user of client computing device 110, or from which a final response is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare-based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for medical record to illustrative medical image translation engine 120 for training a generative model that takes sequences of medical records described by a disease progression model and translates them into an illustrative sequence of corresponding medical images.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements a cognitive system 100 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System P® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. In one embodiment, patient attributes 318 may include identification of a biomedical image for processing to detect anomalies. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 322 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate an illustrative image model, which may be part of the cognitive summary 328. In one embodiment, patient EMR data 322 may include biomedical images. In accordance with the illustrative embodiments, illustrative image model of the cognitive summary 328 is dynamically generated based on historical patient data, such as patient attributes 318 and EMR data 322, and clinical guidelines, which may be incorporated into medical corpus and other source data 326. The treatment regime, which may also be part of the cognitive summary 328, may be presented in a ranked ordering with associated supporting evidence, obtained from the patient attributes 318 and data sources 322-326, indicating the reasoning as to why portions of EMR data 322 are being provided.

In accordance with the illustrative embodiments herein, the healthcare cognitive system 300 is augmented to include medical record to illustrative medical image translation engine 320 for making use of a dual neural machine translation (d-NMT) algorithmic core in order to train a generative model that takes sequences of medical records described by a disease progression model and translates them into an illustrative sequence of corresponding medical images. In one embodiment, illustrative medical image translation engine 320 does this through a generative pathophysiological model that has several parameters and represents conditions for lesions and symptom worsening by changing water levels, mound heights, and bottom slope in a swimming pool. Illustrative medical image translation engine 320 similarly can take a sequence of medical images and produce a translation of the images into a sequence of medical records. It does this through a generative interpreter model that has several parameters and can be used to impute patient medical record measurements that were not taken (and lead to informed follow-up on these by doctors). In both generative models, the parameters are learned by a reinforcement learning algorithm based on the quality of the forward medical image sequence generated (i.e., whether the medical image prognosis model can process it) and the quality of the round trip (i.e., whether the medical record sequence returned by the generative interpreter matches the original sequence). By using a d-NMT algorithm, the advantages of the original algorithm with regard to removing the need for a dual corpus of corresponding sentences in both languages is leveraged here to obviate the need for having extensive corresponding data sets comprising medical records and medical images sampled concurrently from all patients.

Figure 4:
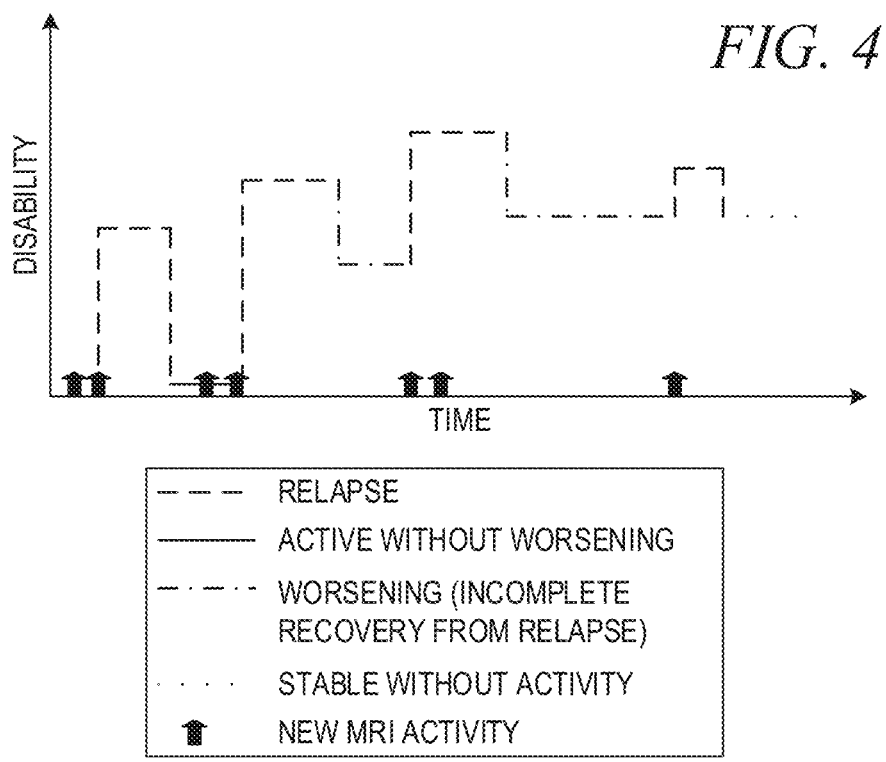
FIG. 4 illustrates a common time course of r-MS plotted in terms of disability (symptomatology)

The problem of illustrating a disease state, its origin, and its likely progression is widespread in the treatment of neurological disorders. Specifically, explaining to patients why a particular condition arises and how it might change over time is important in relapsing-remitting multiple sclerosis (rr-MS) and in neurodegenerative disorders in general. FIG. 4 illustrates a common time course of rr-MS plotted in terms of disability (symptomatology). FIG. 4 shows a progression over time of relapse, active without worsening, worsening, and stable state without activity.

Figure 5:
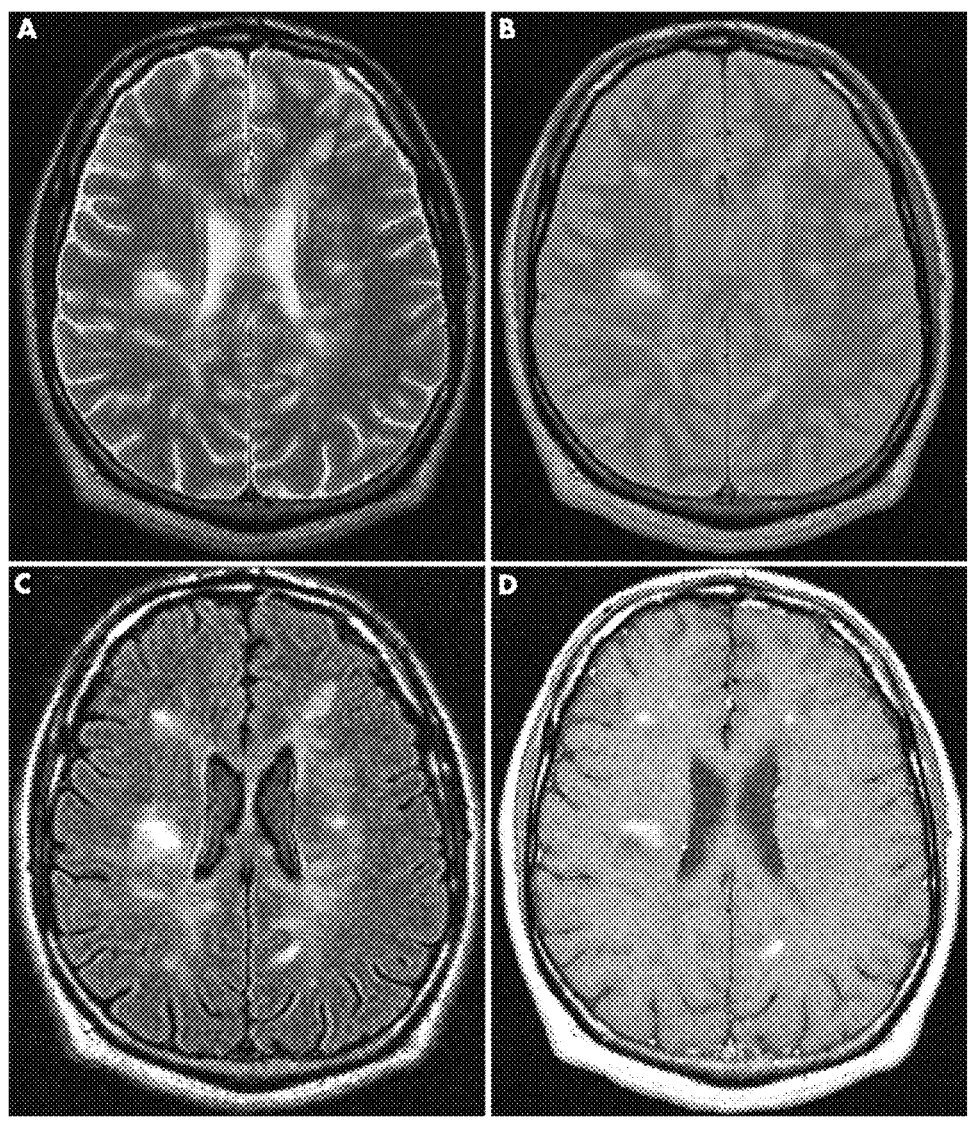
FIG. 5 illustrates an example of medical magnetic resonance imaging activity and lesions.

As in all neurodegenerative disease, the pathophysiological causes of rr-MS are still debated, though clear markers (pale lesions) during advanced flare-ups do appear on medical images. FIG. 5 illustrates an example of medical magnetic resonance imaging activity and lesions. Note that medical magnetic resonance imaging (MRI) activity occurs during relapses in order to investigate the underlying pathophysiology of the relapse (i.e., look for lesions). Patients understand therefore that their disease progression is linked or even caused by lesions.

Figure 6:
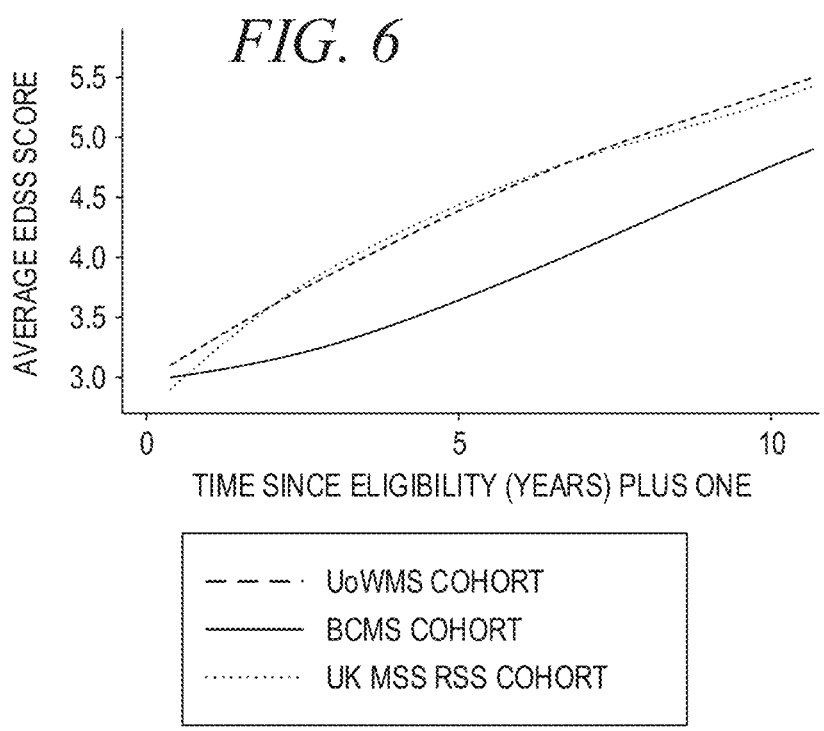
FIG. 6 illustrates an example of Expanded Disability Status Scale (EDSS) scores predicted by a disease progression model based on different patient data sets.

The need, therefore, to illustrate medicine's current understanding of causes and progression to patients in the space of medical imaging is useful, because patients understand these lesions to be correlated with more troubling symptoms. FIG. 6 illustrates an example of Expanded Disability Status Scale (EDSS) scores predicted by a disease progression model based on different patient data sets. A model was developed based on the data set of University of Wales MS (UoWMS), UK (1976), and then cross-validated using British Columbia MS (BCMS) database, Canada (1980).

Figure 7:
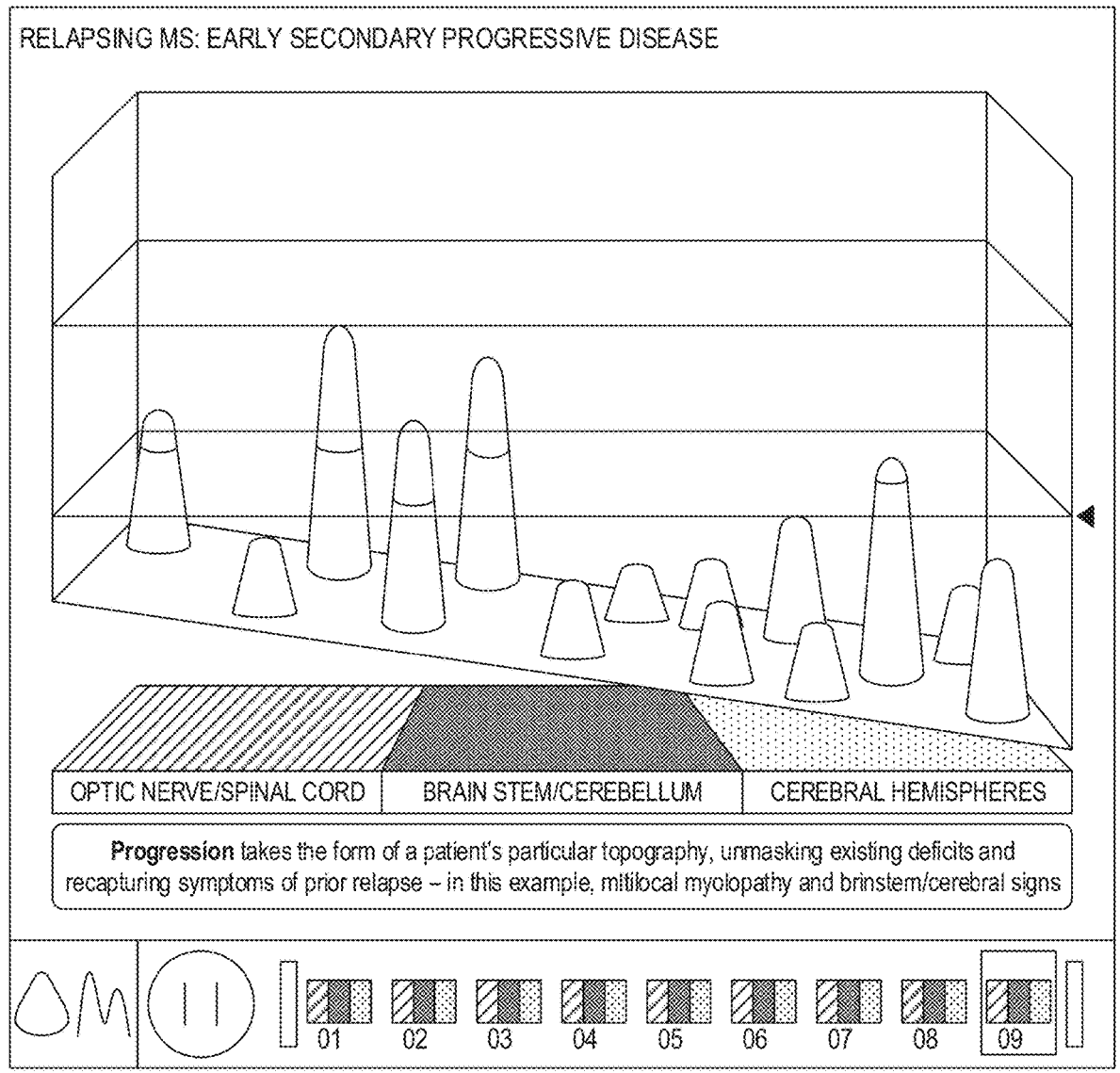
FIG. 7 illustrates the leaking swimming pool model of rr-MS flare-ups in accordance with an illustrative embodiment.

Formally linking sound machine learning based progression models of rr-MS to illustrations of likely lesion progression in the illustrative embodiment using a modified d-NMT system benefits patients and doctors in discussing this disease. FIG. 7 illustrates the leaking swimming pool model of rr-MS flare-ups in accordance with an illustrative embodiment. This illustration of underlying pathophysiology and its dynamics is used to inform patients about the complexity of their disease and what they might expect hypothetically. The illustrative embodiment couples this model to real world evidence based on prediction of patient symptoms (i.e., medical records) with the illustration acting to convey prognosis through simulated medical images. The illustrative embodiment also supports more advanced modeling of likely pathophysiological causes and targets for therapeutic intervention under the same architecture.

Figure 8:
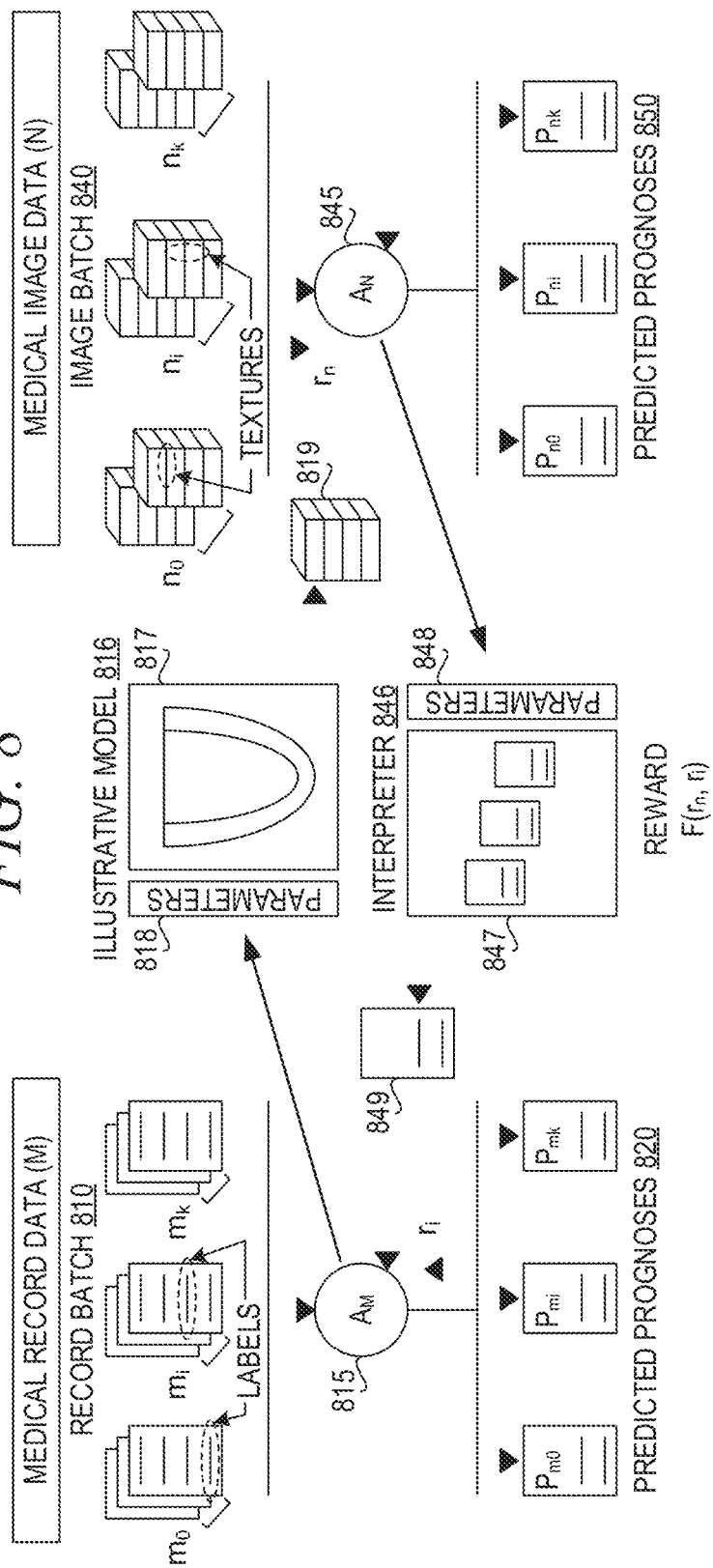
FIG. 8 depicts a dual neural machine translation system to train a medical record to illustrative medical image translation engine in accordance with an illustrative embodiment.

FIG. 8 depicts a dual neural machine translation system to train a medical record to illustrative medical image translation engine in accordance with an illustrative embodiment A first agent 815, $A_M$, is trained to model patient medical records data 810, M, and produce accurate prognoses 820 based on labels also found in M and agent $A_M$'s prognosis model, $\pi_M$. This agent 815 sends a message comprising a record in M to a second agent 845 through a channel (possibly noisy) illustrative generative model 816, $G_{NM}$, which converts the message in M into an illustrative medical image 819 within some imaging modality N. Illustrative generative model 816 includes a parameters-generating model 818 and an image generating model 817. Translation from M to N is achieved by parameterizing and running a physiological model and rendering the model's outputs as a medical image.

A prognosis in this context is a prediction of the next state in the disease progression.

For example, a heart disease progression model acting as $A_M$ produces an accurate prognosis from M. A parameters-generating model 818, $P_M$, provides a second output vector from $A_M$, which is used to parameterize a heart model, which may be an example of an image generating model of the channel illustrative generative model 817, $G_{NM}$. The heart model produces an echocardiogram in N, which is provided to the second agent 845.

The second agent 845, $A_N$, is trained to model medical images 840 in N and produce accurate prognoses 850 based on certain labels provided to it and the second agent's prognosis model, $\pi_N$. Next, second agent 845 receives the medical image 819 in the modality N generated by $G_{NM}$. It checks the generated image 819 and notifies $A_M$ whether it is a natural image in the modality N (note that $A_N$ may not be able to verify the correctness of the translation from M to N because the original medical record is invisible to it).

Next, the second agent 845 sends the received image back to the first agent 815 through another channel (possibly noisy), interpreter model 846, $G_{MN}$, which converts the received medical image 819 from modality N bac to a medical record 849 using another translation model 846 (Note that this translated output may extend the original output vector of $A_N$ beyond the medical record data that $A_N$ was not originally trained with, thus modeling other medical record data that $A_N$ was not originally trained to model.) interpreter model 846 includes parameters-generating model 848 and record generating model 847.

For example, an echocardiogram reading model acting as $A_N$ produces an accurate prognosis from N. A parameters-generating model 848, $P_{NM}$ provides a second output vector from $A_N$, which is used to parameterize a medical record generator 847, $G_{NM}$. The medical record generator produces a complete medical record 849 for the patient, which is then provided to the first disease progression model agent 815 for further analysis.

The game can also be started from the second agent 845 with an original medical image in modality N and then the two agents go through a symmetric process and improve the two channels (generative models) according to the feedback. Playing the game alternately in either direction can improve the illustrative model 816 and interpreter model 846 and permit these models to perform optimally as an illustrative artificial intelligence.

Thus, the illustrative embodiment provides generative adversarial networks (GANs) with combined training of two adversarial neural network components: a first adversarial component: $G_{MN}+A_N$; and a second adversarial component: $G_{NM}+A_M$. In accordance with the illustrative embodiment, the GAN training is modified to accommodate both the rewards generated by $A_N$ and $A_M$ into the loss functions of $G_{MN}$ and $G_{NM}$. In other words, the loss functions of the generative models (i.e., illustrative model 816 and interpreter 846) would account and penalize those generated medical images and reports that are not recognized as mound and believable by $A_N$ and $A_M$, respectively.

The illustrative embodiment also uses reinforcement learning. Total reward of the system at sample: $r_t = (ar_{1,t} +$ br$_{2,t}$)+"discounted future". Standard deep reinforcement learning algorithms, such as Q-learning, can be used to estimate gradients of the loss function and update the parameters p$_{NM}$ and p$_{MN}$ of the illustrative model G$_{MN}$ and interpreter G$_{NM}$.

Training of G$_{MN}$ and G$_{NM}$ proceeds by penalizing mismatches between input data and outcomes of the dual process. In other words, the illustrative embodiment, in which P$_d$ is the actual data distribution, and P$_g$ is the generated data distribution, can exploit the following identity.

$$P_d(N)P_g(M|N,p_{NM}) = P_d(M)P_g(N|M,p_{MN})$$

where p$_{NM}$ and p$_{MN}$ are the parameters of the illustrative model GU and of the interpreter G$_{NM}$, respectively. The constraint on combined probability can be converted into penalty terms of the loss functions for G$_{MN}$ and G$_{NM}$, which are then handled with the method of Langrange multipliers.

The following illustrates the dual-learning algorithm for training the medical record to illustrative medical image translation engine of the illustrative embodiment:

---

1. Input: Medical records data, M, and medical imaging data, N, initial prognosis models, $\pi_M$ and $\pi_N$, generative models G$_{NM}$ and G$_{MN}$, $\alpha$, generative search size K, learning rates $\gamma_{1,t}$, $\gamma_{2,t}$.
2. repeat
3. t = t + 1.
4. Sample medical record and medical image s$_M$ and s$_N$ from M and N respectively.
5. Set s = s$_M$. Model update for the game beginning from M
6. Generate K medical images s$_1$, . . . , s$_K$ using physiological domain model according to parameters generating model P(.|s; G$_{NM}$).
7. for k = 1, . . . , K do
8. Set the parameters generating model reward for the k$^{th}$ sampled medical record as r$_{1,k}$ = $\pi_N$(s$_k$).
9. Set the interpreter reward for the k$^{th}$ sampled sentence as r$_{2,k}$ = logP(s|s$_k$; G$_{MN}$).
10. Set the total reward of the kth sample as r$_k$ = $\alpha$r$_{1,k}$ + (1 − $\alpha$)r$_{2,k}$.
11. end for
12. Compute the stochastic gradient of the parameters of G$_{NM}$:

$$\nabla_{G_{NM}} \hat{E}[r] = \frac{1}{K} \sum_{k=1}^{K} [r_k \nabla_{G_{NM}} \log P(s_k|s; G_{NM})].$$

13. Compute the stochastic gradient of the parameter of G$_{MN}$:

$$\nabla_{G_{NM}} \hat{E}[r] = \frac{1}{K} \sum_{k=1}^{K} [(1 - \alpha) \nabla_{G_{NM}} \log P(s|s_k; G_{NM})].$$

14. Model updates:
G$_{NM}$ ← G$_{NM}$ + $\gamma_{1,t}$$\nabla_{G_{NM}}$$\hat{E}_{[r]}$, G$_{MN}$ + $\gamma_{2,t}$$\nabla_{G_{MN}}$$\hat{E}[r]$.
15. Set s = sN. |> Model update for the game beginning from N.
16. Go through line 6 to line 14 symmetrically.
17. until convergence.

---

The algorithmic core of the illustrative embodiment comprises a disease progression model that operates on medical records to predict a subsequent patient state and medical record as well as a disease progression model that operates on medical images to predict a subsequent patient state and medical images. These next state prediction models are referred to as "prognosis models" and they act in the d-NMT similarly to a language model in a standard d-NMT. The core also comprises generative models that produce a pathophysiological simulation of a patient state given a medical record in order to produce a sequence of medical images as well as an interpretation of a medical image and simulation of a patient state in order to produce a sequence of medical records. In particular, a medical record of symptoms that produces a sequence of medical images is the claim focus for an illustrative artificial intelligence demonstration of likely pathophysiology and dynamics responsible for patient symptom progression.

Figure 9:
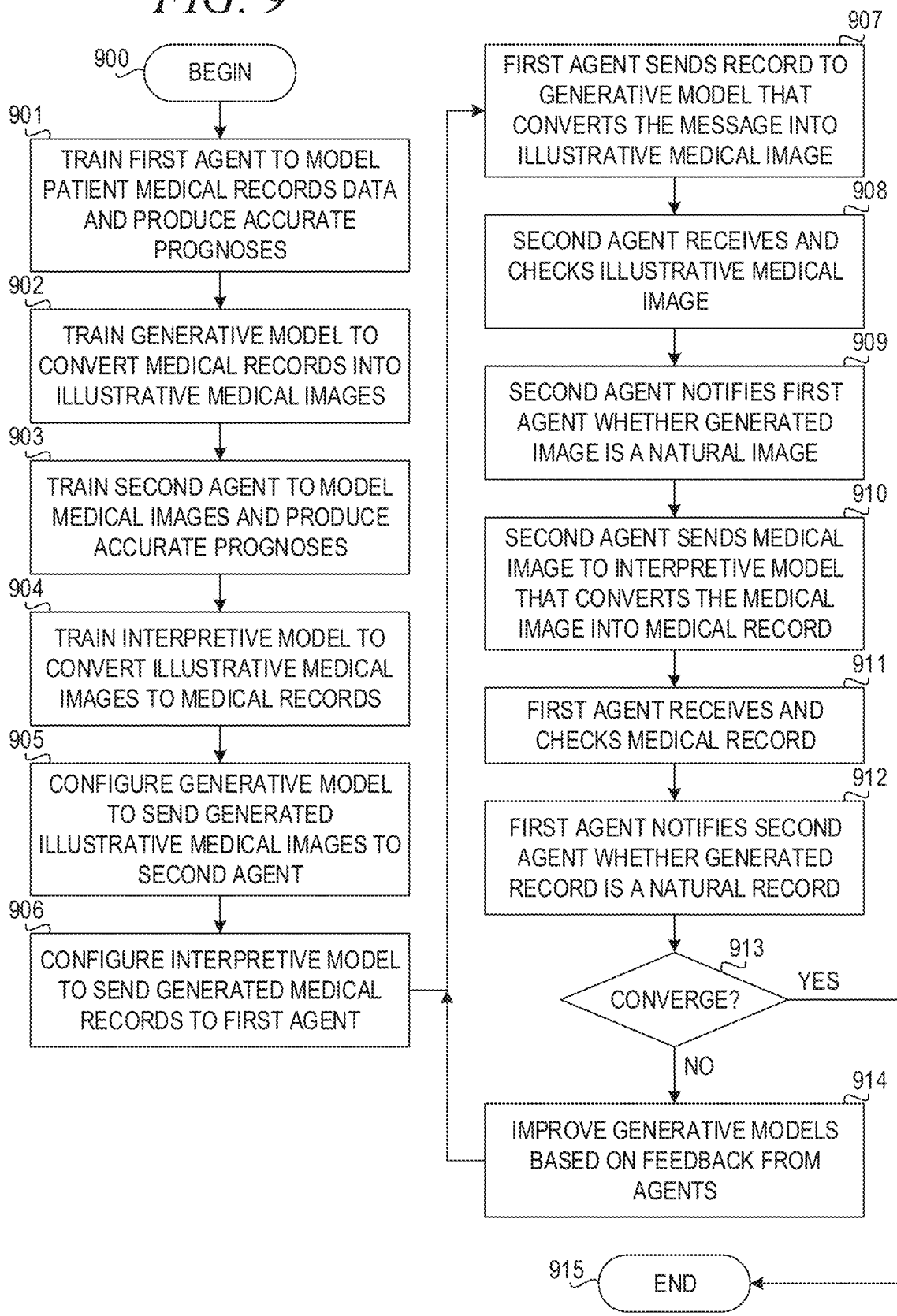
FIG. 9 is a flowchart illustrating training of a medical record to illustrative medical image translation engine in accordance with an illustrative embodiment.

FIG. 9 is a flowchart illustrating a mechanism for training a medical record to illustrative medical image translation engine in accordance with an illustrative embodiment. Operation begins (block 900), and the mechanism trains a first agent to model patient medical records data and produce accurate prognoses (block 901). The mechanism trains a generative model to convert medical records into illustrative medical images (block 902). The mechanism trains a second agent to model medical images and produce accurate prognoses (block 903). The mechanism then trains an interpretive model to convert illustrative medical images to medical records (block 904).

The mechanism configures the generative model to send generated illustrative medical images to the second agent (block 905). The mechanism configures the interpretive model to send generated medical records to the first agent (block 906).

Then, the first agent sends a sequence of medical records to the generative model, which converts the sequence of medical records into an illustrative medical image (block 907). The second agent receives and checks the illustrative medical image to determine whether it is a natural illustrative medical image based on a batch (sequence) of illustrative medical images (block 908). The second agent notifies the first agent of whether the generated image is a natural image (block 909). The second agent is trained to generate a prognosis or next-state image based on the batch of illustrative medical images. Thus, because the second agent uses medical images to perform predict next patient states, the second agent can compare the generated image to the next-state image, or attempt to use the generated image to create a next-state image, to determine whether the generated image is a natural image.

The second agent sends a medical image to an interpretive model, which converts the medical image into a medical record (block 910). The first agent receives and checks the medical record to determine whether it is a natural medical record based on a batch (sequence) of medical records (block 911). The first agent notifies the second agent of whether the generated record is a natural record (block 912). The fast agent is trained to generate a prognosis or next-slate record based on the batch of medical records. Thus, the first agent compares the generated medical record to the next-state medical record to determine whether the generated medical record is a natural record.

Note that the determination of whether the secondly generated medical record is a natural record (in this case, the record evaluated by the first agent) is wholly a function of the similarity of the medical record evaluated by the first agent (and used to parameterize the generative model and create the illustrative medical image) with the medical record returned by the second agent via the generative interpretive model. In this way, the first and second evaluations of naturalness performed by the first and the second agents are different: the first evaluation of naturalness is based on its consistency with prediction of a next patient state based on the input of the generated medical image, and the second evaluation of naturalness is based on the consistency of the returned medical record with what was used to originally parameterize the generative model for creating a medical image.

The mechanism then determines whether the generative model and the interpretive model converge (block 913). The generative model and interpretive model may converge, for example, when both models generate a consecutive number of generated images and records. If the models do not converge, then the mechanism improves the models based on feedback from the agents (block 914), and operation returns to block 907 to repeat the process until the models converge. If the models do converge in block 913, then operation ends (block 915).

Figure 10:
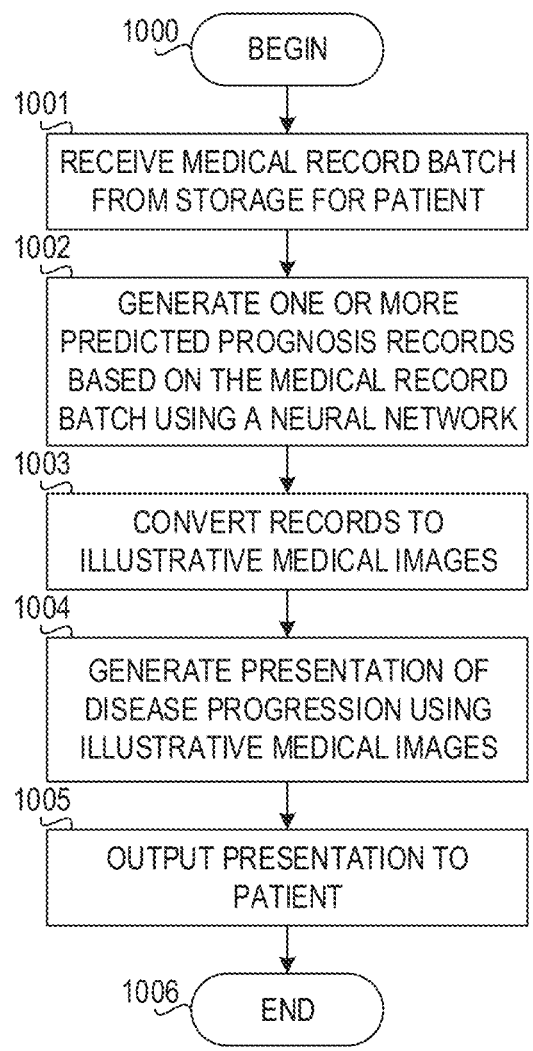
FIG. 10 is a flowchart illustrating operation of a mechanism for medical record to illustrative medical image translation in accordance with an illustrative embodiment.

FIG. 10 is a flowchart illustrating operation of a mechanism for medical record to illustrative medical image translation in accordance with an illustrative embodiment. Operation begins (block 1000), and the mechanism receives a medical record batch from storage for a patient (block 1001). The mechanism generates one or more predicted prognosis records based on the medical record batch using a neural network trained to model patient medical records data (block 1002). The mechanism converts the medical records to illustrative medical images (block 1003). The mechanism then generates a presentation of disease progression using the illustrative medical images (block 1004). The mechanism outputs the presentation to the patient (block 1005). Thereafter, operation ends (block 1006).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM. PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions that are executed by the at least one processor and configure the at least one processor to implement a medical record to illustrative medical image translation engine, the method comprising:
  training the medical record to illustrative medical translation engine using dual neural machine translation to form a generative adversarial network (GAN);
  receiving, by the medical record to illustrative medical image translation engine, a medical record batch from storage for a patient;
  generating, by the medical record to illustrative medical image translation engine, one or more predicted prognosis records based on the medical record batch using a neural network;
  converting, by the medical record to illustrative medical image translation engine, the one or more predicted prognosis records to an illustrative sequence of medical images using a first agent, wherein the illustrative sequence of medical images comprises a leaking swimming pool model of relapsing-remitting multiple sclerosis flare-ups;
  generating, by the medical record to illustrative medical image translation engine, a presentation of disease progression using the illustrative sequence of medical images; and
  outputting, by the medical record to illustrative medical image translation engine, the presentation to a user.

2. The method of claim 1, wherein training the medical record to illustrative medical image translation engine comprises:
  training the first agent to model patient medical records data and produce accurate prognoses; and
  training an illustrative model to convert medical records into illustrative medical images.

3. The method of claim 2, wherein training the medical record to illustrative medical image translation engine further comprises:
  training a second agent to model medical images and produce accurate prognoses; and
  training an interpreter model to convert illustrative medical images to medical records.

4. The method of claim 3, wherein training the medical record to illustrative medical image translation engine further comprises:
  configuring the illustrative model to send generated illustrative medical images to the second agent; and configuring the interpreter model to send generated medical records to the first agent.

5. The method of claim 4, wherein training the medical record to illustrative medical image translation engine further comprises:
sending, by the first agent, a first record to the illustrative model that converts the record to a first illustrative medical image; and
checking, by the second agent, the first illustrative medical image, wherein the second agent notifies the first agent whether the first illustrative medical image is a natural image.

6. The method of claim 5, wherein the first illustrative medical image comprises a parameters-generating model and a generative model.

7. The method of claim 5, wherein training the medical record to illustrative medical image translation engine further comprises:
sending, by the second agent, the first illustrative medical image to the interpreter model that converts the first illustrative medical image to a second medical record; and
checking, by the first agent, the second medical record, wherein the first agent notifies the second agent whether the second medical record is a natural record.

8. The method of claim 7, wherein the interpreter model comprises a parameters-generating model and a record generating model.

9. The method of claim 7, wherein training the medical record to illustrative medical image translation engine further comprises responsive to determining the medical record to illustrative medical image translation engine does not converge, improving the illustrative model and the interpreter model based on feedback from the first agent and the second agent.

10. A computer program product comprising a computer readable storage medium having a computer readable program stored therein, wherein the computer readable program, when executed by a computing device, causes the computing device to implement a medical record to illustrative medical image translation engine, wherein the computer readable program causes the computing device to:
train the medical record to illustrative medical translation engine using dual neural machine translation to form a generative adversarial network (GAN);
receive, by the medical record to illustrative medical image translation engine, a medical record batch from storage for a patient;
generate, by the medical record to illustrative medical image translation engine, one or more predicted prognosis records based on the medical record batch using a neural network;
convert, by the medical record to illustrative medical image translation engine, the one or more predicted prognosis records to an illustrative sequence of medical images using a first agent, wherein the illustrative sequence of medical images comprises a leaking swimming pool model of relapsing-remitting multiple sclerosis flare-ups;
generate, by the medical record to illustrative medical image translation engine, a presentation of disease progression using the illustrative sequence of medical images; and
output, by the medical record to illustrative medical image translation engine, the presentation to a user.

11. The computer program product of claim 10, wherein training the medical record to illustrative medical image translation engine comprises:
training the first agent to model patient medical records data and produce accurate prognoses; and
training an illustrative model to convert medical records into illustrative medical images.

12. The computer program product of claim 11, wherein training the medical record to illustrative medical image translation engine further comprises:
training a second agent to model medical images and produce accurate prognoses; and
training an interpreter model to convert illustrative medical images to medical records.

13. The computer program product of claim 12, wherein training the medical record to illustrative medical image translation engine further comprises:
configuring the illustrative model to send generated illustrative medical images to the second agent; and
configuring the interpreter model to send generated medical records to the first agent.

14. The computer program product of claim 13, wherein training the medical record to illustrative medical image translation engine further comprises:
sending, by the first agent, a first record to the illustrative model that converts the record to a first illustrative medical image; and
checking, by the second agent, the first illustrative medical image, wherein the second agent notifies the first agent whether the first illustrative medical image is a natural image.

15. The computer program product of claim 12, wherein the first illustrative medical image comprises a parameters-generating model and a generative model.

16. The computer program product of claim 14, wherein training the medical record to illustrative medical image translation engine further comprises:
sending, by the second agent, the first illustrative medical image to the interpreter model that converts the first illustrative medical image to a second medical record; and
checking, by the first agent, the second medical record, wherein the first agent notifies the second agent whether the second medical record is a natural record.

17. The computer program product of claim 16, wherein the interpreter model comprises a parameters-generating model and a record generating model.

18. The computer program product of claim 16, wherein training the medical record to illustrative medical image translation engine further comprises responsive to determining the medical record to illustrative medical image translation engine does not converge, improving the illustrative model and the interpreter model based on feedback from the first agent and the second agent.

19. An apparatus comprising:
at least one processor, and
a memory coupled to the at least one processor, wherein the memory comprises instructions, which when executed by the at least one processor, cause the at least one processor to implement a medical record to illustrative medical image translation engine, wherein the instructions cause the at least one processor to:
train the medical record to illustrative medical translation engine using dual neural machine translation to form a generative adversarial network (GAN);

receive, by the medical record to illustrative medical image translation engine, a medical record batch from storage for a patient;

generate, by the medical record to illustrative medical image translation engine, one or more predicted prognosis records based on the medical record batch using a neural network;

convert, by the medical record to illustrative medical image translation engine, the one or more predicted prognosis records to an illustrative sequence of medical images using a first agent, wherein the illustrative sequence of medical images comprises a leaking swimming pool model of relapsing-remitting multiple sclerosis flare-ups;

generate, by the medical record to illustrative medical image translation engine, a presentation of disease progression using the illustrative sequence of medical images; and output, by the medical record to illustrative medical image translation engine, the presentation to a user.

20. The apparatus of claim 19, wherein training the medical record to illustrative medical image translation engine comprises:

training the first agent to model patient medical records data and produce accurate prognoses;

training an illustrative model to convert medical records into illustrative medical images;

training a second agent to model medical images and produce accurate prognoses;

training an interpreter model to convert illustrative medical images to medical records;

configuring the illustrative model to send generated illustrative medical images to the second agent;

configuring the interpreter model to send generated medical records to the first agent;

sending, by the first agent, a first record to the illustrative model that converts the record to a first illustrative medical image;

checking, by the second agent, the first illustrative medical image, wherein the second agent notifies the first agent whether the first illustrative medical image is a natural image;

sending, by the second agent, the first illustrative medical image to the interpreter model that converts the first illustrative medical image to a second medical record;

checking, by the first agent, the second medical record, wherein the first agent notifies the second agent whether the second medical record is a natural record; and responsive to determining the medical record to illustrative medical image translation engine does not converge, improving the illustrative model and the interpreter model based on feedback from the first agent and the second agent.

* * * * *